US 7,405,325 B2

(12) United States Patent
Göttel et al.

(10) Patent No.: US 7,405,325 B2
(45) Date of Patent: Jul. 29, 2008

(54) PROCESS FOR THE PREPARATION OF 4-HYDROXALKYLAMINO-2-NITRO-ANISOLES

(75) Inventors: Otto Göttel, Marly (CH); Emmanuel Morand, Villars-sur-Glâne (CH); Hans-Jürgen Braun, Ueberstorf (CH)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/788,064

(22) Filed: Apr. 19, 2007

(65) Prior Publication Data

US 2007/0249868 A1    Oct. 25, 2007

(30) Foreign Application Priority Data

Apr. 20, 2006    (EP) .................................. 06008163

(51) Int. Cl.
*C07C 211/00* (2006.01)
(52) U.S. Cl. .................................................... 564/305
(58) Field of Classification Search ........................ None
See application file for complete search history.

(56) References Cited

U.S. PATENT DOCUMENTS 5,508,467 A * 4/1996 Bauer et al. ................. 564/412

FOREIGN PATENT DOCUMENTS

DE    3536066 A1    4/1986
DE    3806237 C1    10/1989

OTHER PUBLICATIONS

European Search Report, Application No. 06008163.5, dated Oct. 13, 2006 (4 pages).

\* cited by examiner

*Primary Examiner*—Yvonne Eyler
*Assistant Examiner*—Jennifer Y Cho
(74) *Attorney, Agent, or Firm*—Idris N. McKelvey

(57) ABSTRACT

A process for the preparation of 4-hydroxyalkylamino-2-nitro-anisoles of the general formula (I)

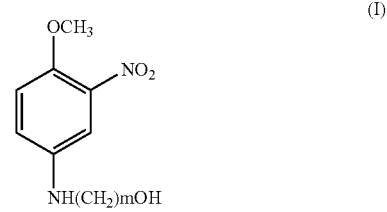

wherein m is 2 or 3;
by reaction of a 4-halogeno-3-nitro-aniline of formula (II) with a chloroalkyl-chloroformate of formula (III), alkaline ring closure of the resulting carbamate and nucleophilic replacement of the halogeno atom by a methoxy group to form a derivative of formula (IV), and finally ring opening of the resulting cyclic carbamate by treatment with methanolic alkali metal hydroxide, followed by neutralization with inorganic or organic acids, wherein the complete reaction is executed in a non-aqueous medium; as well as process for the preparation of 2-amino-4-hydroxyalkylamino-anisoles of formula (V)

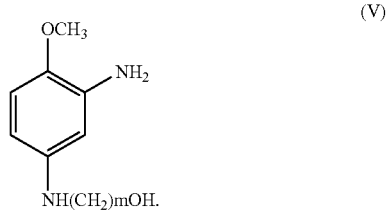

8 Claims, No Drawings

PROCESS FOR THE PREPARATION OF 4-HYDROXALKYLAMINO-2-NITRO-ANISOLES

FIELD OF THE INVENTION

The present invention relates to a new process for the preparation of 4-hydroxyalkyl-amino-2-nitro-anisoles, which are useful as intermediates for the synthesis of hair dye couplers such as 4-hydroxyalkylamino-2-amino-anisoles.

BACKGROUND OF THE INVENTION

German Patent Application No. 38 06 237 describes a process for the preparation of N4-substituted 1-methoxy-2, 4-diaminobenzenes by the reaction of 4-amino-2-nitro-anisole with chloroalkyl-chloroformates in different aqueous solvent mixtures containing a buffer. Reactions are carried out in a temperature range from about 70° C. to the reflux temperature of the solvents or solvent mixtures used; reaction times between about 4 and about 12 hours are required. The open chain carbamates are isolated by addition of water. Further steps are carried out in strong basic aqueous media, which is completely unfavorable in terms of the presence of 4-amino-2-nitro-anisole.

German Patent Application No. 35 36 066 describes a multi-step process for the preparation of N,N'-disubstituted p-phenylenediamines by reacting a 4-halogen-3-nitro-aniline with a β-chloroethyl-chloroformate and forming an oxazolidone by addition of an alkali metal hydroxide in an organic solvent, then condensing the oxazolidone with a primary amine and at the end alkaline hydrolysis of the reaction product.

Problems concerning 4-amino-2-nitro-anisole residues have also been described in U.S. Pat. No. 5,508,467, which relates to a process for the preparation of hydroxyalkylamino-nitro-benzenes. Although U.S. Pat. No. 5,508,467 teaches that highly pure products can be provided by this process, the amount on residual 4-amino-2-nitro-anisole, which is 480 ppm, is still unsatisfactory. The 4-amino-2-nitro-anisole cannot entirely be removed by multiple recrystallization without considerable loss in yield. If the target nitro compounds would be reduced into the corresponding amines, it would therefore be impossible to separate the resulting 2,4-diaminoanisole by-product from the target compounds.

So it is essential to find a process for the synthesis of 4-hydroxyalkylamino-2-nitro-anisoles which gives extremely low amounts of residual 4-amino-2-nitro-anisole, because to be used as intermediate for the synthesis of hair dye precursors 4-hydroxyalkylamino-2-nitro-anisoles must contain significantly lower amounts of 4-amino-2-nitro-anisole than feasible by the methods known in the state of the art.

SUMMARY OF THE INVENTION

The object of the present invention therefore is to provide a process, which resolves the problems of remaining residual 4-amino-2-nitro-anisole efficiently.

It has now been found that the problem described above is resolved by a process according to our invention.

DETAILED DESCRIPTION OF THE INVENTION

The present invention relates to a new process for the preparation of 4-hydroxyalkyl-amino-2-nitro-anisoles of the general formula (I) as described in the below-mentioned scheme I

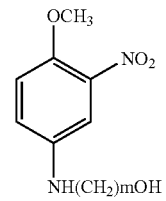

wherein m is 2 or 3;

by reaction of 4-halogeno-3-nitro-anilines of formula (II) with chloroalkyl-chloroformates (III), alkaline ring closure of the carbamates and nucleophilic replacement of the halogeno atoms by a methoxy group to form derivatives of formula (IV), and finally ring opening of the resulting cyclic carbamates by treatment with methanolic alkali metal hydroxide, followed by neutralization with an inorganic or organic acid, wherein the complete reaction is executed in a non-aqueous medium.

Scheme 1: Synthesis of of 4-hydroxyalkylamino-2-nitro-anisoles of formula (I)

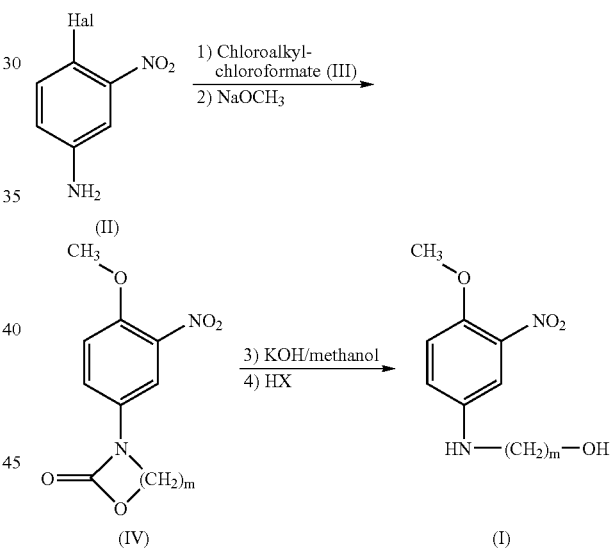

The resulting 4-hydroxyalkylamino-2-nitro-anisoles are important intermediates for the preparation of 2-amino-4-hydroxyalkylamino-anisoles and their salts, which are useful as dye precursors for the oxidative hair colouring.

4-Halogeno-3-nitro-anilines of formula (II) like 4-chloro-3-nitro-aniline or especially 4-fluoro-3-nitro-aniline are reacted with chloroalkyl-chloroformates (III)—preferably in inert dipolar aprotic solvents as dimethylformamide, dimethylacetamide or N-methyl-pyrrolidone—whereby condensation occurs spontaneously. Due to the temperature increase, external cooling is required. The reaction may be conducted between room temperature and the boiling point of the used solvents, but with respect to high product purities, temperature should be from about 40° C. to about 60° C. Due to the very high selectivity of the reaction the resulting reaction product can be used in the next step without any isolation or purification.

In the following step of the synthesis, alkali methoxide is added to the reaction mixture to form the cyclic carbamates; preferably a commercial solution of 30% sodium methoxid in methanol is used. By addition of three equivalents of alkali methoxide the anisole structure is formed by nucleophilic displacement of the aromatic halogeno atom. The addition of the sodium methoxide solution leads to a further temperature increase, so reaction is also conducted under external cooling in the same temperature range (preferably from about 40° C. to about 60° C.) as described for the initial step.

Ring opening to the target compounds of formula (I) is carried out by treatment with alkali metal hydroxide. Preferably a methanolic solution of alkali metal hydroxides, for example, sodium hydroxide or potassium hydroxide, is used.

At the end of the reaction the alkali amount is neutralized by adding one equivalent of an inorganic or organic acid related on the alkali hydroxide amount. When using methanol as solvent, the use of acetic acid is preferred. The final ring opened products precipitate as yellow-orange products by the addition of water.

If necessary, the compound of the structure (I) which contains the hydroxyethyl group, can be recrystallized from solvents like toluene or xylene, whereby adsorbents like activated charcoal or activated diatomaceous earth (Hyflo, Diatomeen) may be used.

Compared to the method described in German Patent No. 35 36 066 the initial condensation step of the synthesis according to our invention is carried out under milder conditions without external heating and without addition of any base. Furthermore in comparison to the method described in German Patent No. 38 06 237 and U.S. Pat. No. 5,508,467 the synthesis according to our invention offers a faster and very selective ring opening reaction to the corresponding hydroxyalkyl anilines.

The process according to the present invention provides N-(2-hydroxalkyl)-4-methoxy-3-nitro-anilines with an extremely low content of 4-amino-2-nitro-anisole. A further advantage is that three steps, namely the condensation of the halogeno-nitro-anilines with the chloroalkyl-chloroformates, the ring closure to cyclic carbamates and the displacement of the aromatic halogeno atom can be carried out without isolation of the intermediates. The reaction steps are conducted in non-aqueous systems which in contrast to processes known from the art provide highly pure products. The high purity is essential when the products of formula (I) are used as intermediates for the preparation of hair dye couplers, which can be obtained by reduction of the nitro group to the corresponding amines.

Hence another object of the present invention is a process for the synthesis of 2-amino-4-hydroxyalkylamino-anisoles of formula (V),

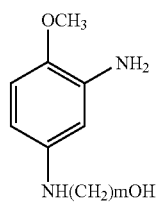
(V)

wherein m is 2 or 3;

by reaction of 4-halogeno-3-nitro-anilines of formula (II) with chloroalkyl-chloroformates (III), alkaline ring closure of the carbamates and nucleophilic replacement of the halogeno atoms by a methoxy group to form derivatives of formula (IV), ring opening of the resulting cyclic carbamates by treatment with methanolic alkali metal hydroxide, followed by neutralization with inorganic or organic acids, wherein the complete reaction is executed in a non-aqueous medium, and finally reduction of the nitro group of the resulting 4-hydroxyalkyl-amino-2-nitro-anisoles of formula (I) to the corresponding amines of formula (V) and their adducts with an organic or inorganic acid.

The reduction of the nitro compounds of formula (I) may be carried out by reductive methods well known from literature, for example, a catalytic hydrogenation with hydrogen and a Pd/C catalyst.

The following examples will explain the subject matter of the invention in greater detail without limiting its scope to these examples.

EXAMPLES

Example 1

Preparation of
N-(2-hydroxyethyl)-4-methoxy-3-nitro-aniline

Step 1.1:
3-(4-Methoxy-3-nitrophenyl)-1,3-oxazolidine-2-one

4-Fluoro-3-nitro-aniline (50.0 g) is dissolved in 100 ml N-methyl-pyrrolidone. Subsequently 2-chloroethyl-chloroformate (48.1 g) is added dropwise under external cooling, whereupon the internal temperature is kept below 60° C. After completion of the addition stirring is continued for 30 minutes and then a 30% methanolic sodium methoxide solution (230.7 g) is added dropwise in such a rate that under external cooling the temperature remains below 40° C. When the addition is completed, the reaction mixture is allowed to cool and then poured into cold water (2000 ml) and stirred for additional 30 minutes. The obtained suspension is filtered off, washed with water, and dried.

Yield: 62.3 g yellowish solid.
$^1$H-NMR (DMSO-d$_6$/300 MHz): δ=8.13 (s, 1H), 7.81 (d, 1H), 7.42 (d, 1H), 4.46 (t, 2H), 4.08
(t, 2H), 3.92 ppm (s, 3H).

Step 1.2:
N-(2-Hydroxyethyl)-4-methoxy-3-nitro-aniline

Solid potassium hydroxide (3.5 g) is dissolved in methanol (100 ml). To the obtained solution the 3-(4-methoxy-3-nitrophenyl)-1,3-oxazolidin-2-one of step 1.1 (5 g) is added whereupon a yellow suspension is formed. Then the reaction mixture is heated under reflux for 5 hours and a red solution is obtained. With stirring, diluted acetc acid (3.7 g in 20 ml water) is added dropwise to the warm solution and the reaction mixture is cooled down to from about 0° C. to about 5° C. An orange suspension is obtained, which is filtered. The resulting solid is dried.

Yield: 3.7 g.
$^1$H-NMR (DMSO-d$_6$/300 MHz): δ=7.13 (d, 1H); 7.02 (d, 1H); 6.92 (dd, 1H); 5.75 (t, 1H); 4.71 (t, 1H); 3.54 (m, 2H); 3.40 (s, 3H); 3.08 ppm (m, 2H).

Example 2

Preparation of
N-(3-hydroxypropyl)-4-methoxy-3-nitro-aniline

4-Fluoro-3-nitro-aniline (20.0 g) is dissolved in 100 ml dimethylacetamide. Then 3-chloropropyl-chloroformate (22.12 g) is added dropwise within 30 minutes under external cooling to keep the reaction temperature below 60° C. After the addition is completed, the reaction mixture is allowed to cool. Then a 30% methanolic solution of sodium methoxide (92.3 g) is added dropwise. The rate of addition and external cooling is adjusted to maintain an internal temperature of from about 60° C. to about 70° C. When the temperature rise ceases, the reaction mixture is poured into 200 ml water, neutralized with 2n sulfuric acid, and extracted twice with 400 ml ethylacetate. The combined organic layers are dried over sodium sulphate, filtered, and evaporated to dryness.

Yield: 18.8 g of a viscous reddish product.

$^1$H-NMR (DMSO-$d_6$/300 MHz): δ=7.13 (d, 1H); 6.97 (d, 1H); 6.87 (dd, 1H); 5.75 (t, 1H); 4.50 (t, 1H); 3.78 (s, 3H); 3.49 (m, 2H); 3.03 (m, 2H); 1.67 ppm (m, 2H).

No 4-Amino-2-nitro-anisole is detected by HPLC (detection limit 10 ppm).

Unless stated otherwise, all of the percentages given in the present application are percentages by weight.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for the preparation of 4-hydroxyalkylamino-2-nitro-anisoles of the general formula (I)

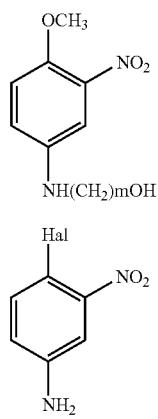

(I)

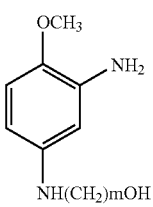

(II)

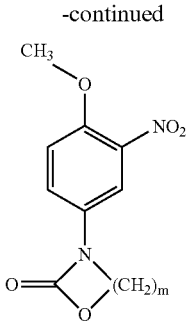

(IV)

wherein m is 2 or 3;

wherein a 4-halogeno-3-nitro-aniline of formula (II) is caused to react with a chloroalkyl-chloroformate, followed by an alkaline ring closure of the resulting carbamate and a nucleophilic replacement of the halogeno atom by a methoxy group to form a derivative of formula (IV), and then followed by a ring opening of the resulting cyclic carbamate by a treatment with methanolic alkali metal hydroxide, and finally followed by a neutralization with an inorganic or organic acid, wherein the complete reaction is executed in a non-aqueous medium.

2. A process according to claim 1, wherein said 4-halogeno-3-nitro-aniline of formula (II) is a 4-chloro-3-nitro-aniline or a 4-fluoro-3-nitro-aniline.

3. A process according to claim 1, wherein said non-aqueous medium is an inert dipolar aprotic solvent.

4. A process according to claim 1, wherein the first two reaction steps are performed at a temperature of from about 40° C. to about 60° C.

5. A process according to claim 1, wherein said nucleophilic replacement of the halogeno atom is carried out with 3 equivalents of alkali methoxide per equivalent of said derivative of formula (IV).

6. A process according to claim 1, wherein said alkali metal hydroxide is a sodium hydroxide or a potassium hydroxide.

7. A process for the preparation of 2-amino-4-hydroxyalkylamino-anisoles of the general formula (V)

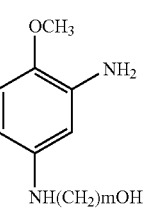

(V)

wherein m is 2 or 3;

wherein the process according to claim 1 is followed by a reduction of said 4-hydroxyalkylamino-2-nitro-anisole of formula (I).

8. A process according to claim 7, wherein a catalytic hydrogenation is used for the reduction of said 4-hydroxyalkylamino-2-nitro-anisole of (I).

* * * * *